United States Patent [19]

Chiba et al.

[11] 3,962,296

[45] June 8, 1976

[54] PROCESS FOR THE PREPARATION OF STABILIZERS FOR SYNTHETIC RESINS

[75] Inventors: Tetsuo Chiba; Yoshio Itoh, both of Yokohama; Satoshi Makabe, Ninomiya, all of Japan

[73] Assignee: Sankyo Organic Chemicals Co., Ltd., Kawasaki, Japan

[22] Filed: Apr. 29, 1975

[21] Appl. No.: 572,848

Related U.S. Application Data

[63] Continuation-in-part of Ser. No. 499,203, Aug. 21, 1974, abandoned.

[30] Foreign Application Priority Data

Oct. 11, 1973 Japan.............................. 48-113239

[52] U.S. Cl. ............................................. 260/429.7
[51] Int. Cl.$^2$.......................................... C07F 7/22
[58] Field of Search................................. 260/429.7

[56] References Cited
UNITED STATES PATENTS
2,727,917  12/1955  Mack et al...................... 260/429.7

OTHER PUBLICATIONS
Sasin et al., J. Org. Chem., vol. 20, pp. 387–390 (1955).

*Primary Examiner*—Helen M. S. Sneed
*Attorney, Agent, or Firm*—Flynn & Frishauf

[57] ABSTRACT

A process for the preparation of a stabilizer for synthetic resins mainly consisting of a molecular weight increased alkyltin mercaptocarboxylic acid ester which comprises interesterification between a corresponding lower molecular weight alkyltin mercaptocarboxylic acid ester and an alcohol is disclosed.

11 Claims, No Drawings

PROCESS FOR THE PREPARATION OF STABILIZERS FOR SYNTHETIC RESINS

This is a continuation-in-part of application Ser. No. 499,203 filed Aug. 21, 1974, now abandoned.

BACKGROUND OF THE INVENTION

1. Field of the invention

This invention relates to a process for the preparation of a stabilizer for synthetic resins such as a chlorine-containing resin, acrylonitrile — butadiene — styrene copolymer, methyl methacrylate — butadiene — styrene copolymer and the like. In particular, this invention relates to a process for the preparation of a stabilizer for synthesic resins mainly consisting of a molecular weight increased alkyltin mercaptocarboxylic acid ester having little odor and being excellent in lubricating effect which comprises interesterification between a certain alkyltin mercaptocarboxylic acid ester and an alcohol.

2. Description of the prior art

In general, such synthetic resins as chlorine-containing resin, acrylonitrile — butadiene — styrene copolymer, methyl methacrylate — butadiene — styrene copolymer and the like, especially a vinyl chloride resin, are liable to be deteriorated with either heat or light. Heretofore, there have been employed a number butadiene stabilizers, for example, inorganic metal salts such as tribasic lead sulfate, metal soaps such as cadmium stearate, barium stearate, lead stearate, calcium stearate and zinc stearate, metal salts of substituted phenols such as barium nonylphenolate, organo tin compounds such as an alkyltin laurate, an alkyltin maleate and an alkyltin mercaptocarboxylic acid ester, epoxy compounds such as an epoxy resin and an epoxidated oil, phenol-like compounds and organic esters of phosphorus acid, for the purposes of preventing the aforementioned deteriorations occuring in processing these resins and in the use of the obtained product. Particularly, alkyltin mercaptocarboxylic acid esters are more excellent in either heat-stabilizing effect or in transparency so that glassy product can be obtained. These conventional esters, therefore, have been tested for the purpose of the application to the processing of such resins. However, these conventional esters emit unpleasant mercaptan odor in the manufacture which terribly lowers the working environment. Further, such unpleasant mercaptan odor remains on the obtained moulded product such as a film, sheet, bottle and the like, and which lowers the value of the products. In addition, conventional alkyltin mercaptocarboxylic acid esters can hardly bring about lubricant effect into the resins, and therefore a large amount of lubricants are compounded for the purpose of lubricating. Improvements in the odor and the lubricating effect have been, heretofore, contemplated by elevating boiling points of such alkyltin mercaptocarboxylic acid esters by way of increasing the molecular weight of an alkyltin mercaptocarboxylic acid esters.

In general, the molecular weight of an alkyltin mercaptocarboxylic acid ester may be increased by having the molecular weight of a mercaptocarboxylic acid ester portion increased. The molecular weight of the mercaptocarboxylic acid ester may be increased through employing either a higher molecular weight mercaptocarboxylic acid or a higher molecular weight alcohol. Generally, employment of a higher molecular weight alcohol may be effective in increasing the molecular weight of the mercaptocarboxylic acid ester.

It is well known that either ester formation by reaction of an acid with an alcohol or interesterification is conducted in the presence of an acid or base catalyst. Further, it is known that the employed catalyst is necessarily removed from the stabilizer because such a catalyst may be almost harmful to a resin in which the stabilizer is incorporated. Separation of the catalyst from the resulting ester may preferably be effected by distillation of the ester after washing with water, and, for this reason, the resulting ester preferably has a low boiling point. At least, the resulting ester must be distillable at a reduced pressure. Accordingly, the ester formation has, heretofore, been effected so as to yield a higher molecular weight mercaptocarboxylic acid ester in advance of formation of its tin compound, as disclosed in U.S. Pat. Nos. 2,641,596 2,648,650, 2,752,325 and 3,832,750.

However, a molecular weight increased mercaptocarboxylic acid ester has a rather higher boiling point, and the resulting ester is partly decomposed during the distillation at an elevated temperature. The decomposed esters generally impart malodor to the resin in which the stabilizer is incorporated.

The ester formed by the reaction may be employed as the stabilizer without purification, but crude one inevitably imparts malodor to the resin.

SUMMARY OF THE INVENTION

Accordingly, it is an object of this invention to provide a process for the preparation of a stabilizer for synthetic resins which has little odor. Another object of this invention is to provide a process for the preparation of a stabilizer in good yield. A further object is to provide a stabilizer for synthetic resins which has little odor. A still further object is to provide a process for the preparation of an alkyltin mercaptocarboxylic acid ester having an increased molecular weight. Other objects of this invention will be understood with reference to the content of the present specification.

These and other objects of this invention have been attained by a process for the preparation of a stabilizer for synthetic resins mainly consisting of a molecular weight increased alkyltin mercaptocarboxylic acid ester which comprises reaction of an alkyltin mercaptocarboxylic acid ester having the formula selected from the group consisting of

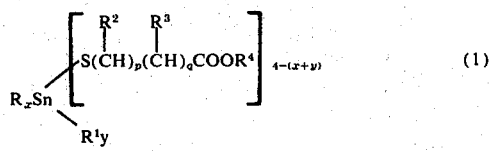  (1)

  (2)

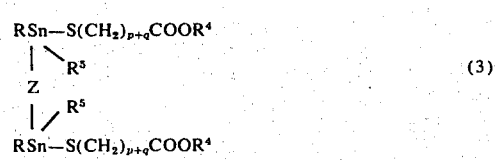  (3)

in which R represents an aliphatic alkyl group having 1–12 (preferably 1–8) carbon atoms or a phenyl group; R¹ represents an aliphatic alkylthio group having 8–18

(preferably 8–12) carbon atoms, an aliphatic alkanoyloxy group having 8–18 (preferably 8–12) carbon atoms, a residue of monoalkylester of maleic acid in which the alkyl is an aliphatic alkyl containing 8–18 (preferably 8–12) carbon atoms or a benzoyloxy group; $R^2$ and $R^3$ are the same or different and each represents hydrogen, an aliphatic alkyl group having 1–4 (preferably one) carbon atoms or a phenyl group; $R^4$ represents an aliphatic alkyl group having 1–8 carbon atoms or an aliphatic alkoxyalkyl group having 3–6 carbon atoms; $R^5$ represents an aliphatic alkyl group having 1–12 (preferably 4–8) carbon atoms, an aliphatic alkanoyloxy group having 8–10 carbon atoms or a $—S(CH_2)_{p+q}COOR^4$ group; $x$ and $y$ represent integers of 1 to 3 and 0 to 1, respectively, in which $x+y$ is up to 3 inclusive; $p$ and $q$ represent integers of 1 to 2 and 0 to 1, respectively; and Z represents oxygen, sulfur or a divalent maleic acid residue (a residue obtained from maleic acid by removal of the terminal two hydrogens), with a monovalent aliphatic alcohol having 4–18 (preferably 12–18) carbon atoms, a divalent aliphatic alcohol having 2–6 carbon atoms or an aliphatic alkoxyalkyl alcohol having 4–10 carbon atoms, the boiling point of said alcohol being higher than that of an alcohol having the formula $R^4OH$, in which $R^4$ is the same as above, by at least 30°C, at a temperature of 100° to 200°C in the absence of a catalyst, with removal of the lower boiling alcohol produced.

DETAILED DESCRIPTION OF THE PREFERRED ENBODIMENTS

In view of the state of the prior art as described hereinbefore, the present inventors have made various studies on the preparation of the molecular weight increased alkyltin mercaptocarboxylic acid ester, and found out that interesterification between an alkyltin mercaptocarboxylic acid ester containing a lower molecular weight alcohol portion and a higher molecular weight alcohol is readily carried out in the absence of a catalyst. In other words, the alkyltin mercaptocarboxylic acid ester itself likely acts as a catalyst in the interesterification reaction.

It was previously disclosed in Japanese Patent Gazettes, Publn. Nos. 45-29673/1970, 46-485/1971 and 46-19944/1971, that certain organotin compounds are effective as catalysts in an esterification reaction or an interesterification reaction of a carboxylic acid or a carboxylic acid ester with an alcohol. Yet, there has not been reported an interesterification of an alkyltin mercaptocarboxylic acid ester, and it has not been known that such an alkyltin mercaptocarboxylic acid ester is effective as a catalyst in the interesterification reaction.

The present inventors have tried to examine whether or not most of organotin compounds are likewise effective as the catalyst in interesterification reaction. Some of these results are shown below.

3-Mercaptopropionic acid (1mol) and 2-ethylhexyl alcohol (1 mol) were caused to react at 135°C for 5 hours, with removal of the resulting water, by employing dibutyltin oxide in the proportion of 0.1% (by weight) based on the former acid to give the esterification ratio of 66%. Methyl 3-mercaptopropionate (1 mol) and 2-ethylhexyl alcohol (1 mol) were caused to react at 140°C for 5 hours, with removal of the resulting methanol, by employing dibutyltin oxide in the proportion of 0.1% (by weight) based on the former ester to give the interesterification ratio of 20%. Further, both of the reactions were continued for additional 3 hours to fail in increase of the esterification ratio and the interesterification ratio and to result in giving yellow brown reaction solutions.

On the other hand, the esterification reaction of 3-mercaptopropionic acid (1 mol) with 2-ethylhexyl alcohol (1 mol) using sulfuric acid as a catalyst in the proportion of 0.1% (by weight) based on the former acid which was carried out at 135°C for 5 hours, with removal of the resulting water, gave the esterification ratio of 68%. The interesterification reaction between methyl 3-mercaptopropionate (1 mol) and 2-ethylhexyl alcohol (1 mol) using sulfuric acid as a catalyst in the proportion of 0.1% (by weight) based on the former ester which was carried out at 140°C for 5 hours, with removal of the resulting methanol, gave the interesterification ratio of 45%. Further, both of the reactions were continued for additional 3 hours to fail in increasing the esterification ratio and the interesterification ratio and to result in giving yellow brown reaction solutions.

As seen from the above-mentioned results, in both the esterification reaction of mercaptocarboxylic acids with alcohols and the interesterification reaction between mercapto carboxylic acid esters and alcohols, the usual organotin compounds such as dialkyltin oxides are less effective than either of p-toluene-sulfonic acid or sulfuric acid in either promoting the reaction rate or the esterification or interesterification ratio. As the result, the present inventors have failed to prove the assumption that usual organotin compounds are analogously effective as catalysts in either esterification of a mercaptocarboxylic acid or interesterification of a mercaptocarboxylic acid ester.

In contrast with the above-mentioned results, the reaction in the process of the present invention showed the extremely fast reaction rate and further showed the prominent interesterification ratio, for example, more than 90%. Moreover, the obtained alkyltin mercaptocarboxylic acid esters were pale yellow and had very little odor.

In the aforementioned formulae (1), (2) and (3), R represents an aliphatic alkyl group having 1–12 carbon atoms e.g., methyl, ethyl, propyl, n-butyl, isobutyl, n-pentyl, isopentyl, n-hexyl, isohexyl, n-heptyl, isoheptyl, n-octyl, 2-ethylhexyl, isooctyl, nonyl, decyl, undecyl and dodecyl, or a phenyl group. $R^1$ represents an aliphatic alkylthio group having 8–18 carbon atoms, e.g., n-octylthio, isooctylthio, laurylthio and stearylthio, an aliphatic alkanoyloxy group having 8–18 carbon atoms, e.g., caproyloxy, capryloxy, lauroyloxy, and stearoyloxy, a residue of monoalkylester of maleic acid in which the alkyl is an aliphatic alkyl containing 8–18 carbon atoms, e.g., n-octyl, 2-ethylhexyl, isooctyl, decyl, lauryl, stearyl and oleyl esters of maleic acid, or a benzoyloxy group. $R^2$ and $R^3$ are the same or different and each represents hydrogen, an aliphatic alkyl group having 1–4 carbon atoms, e.g., methyl, ethyl, propyl, isopropyl, n-butyl and isobutyl, or a phenyl group. $R^4$ represents an aliphatic alkyl group having 1-8 carbon atoms, e.g., methyl, ethyl, propyl, isopropyl, n-butyl, isobutyl, pentyl, hexyl, heptyl, n-octyl, isooctyl and 2-ethylhexyl or an aliphatic alkoxyalkyl group having 3–6 carbon atoms, e.g., methoxyethyl, ethoxyethyl, methoxybutyl and ethoxybutyl. $R^5$ represents an aliphatic alkyl group having 1–12 carbon atoms, e.g., methyl, ethyl, n-propyl, n-butyl, hexyl, octyl, decyl and dodecyl, a $—S(CH_2)_{p+q}COOR^4$ group, e.g., (methyl mercaptoacetate), (butyl mercaptoacetate) and (2- ethylhexyl 3-mercaptopropionate), or an aliphatic alkanoyloxy group having 8–18 carbon atoms, e.g., caproyloxy, capryloxy, lauroyloxy and stearoyloxy.

The starting compound represented by the formula (1) may be exemplified by:
monobutyltin tris(isooctyl mercaptoacetate), BuSn(SCH$_2$COO·iso-Oct)$_3$
monobutyltin tris(methyl 3-mercaptopropionate), BuSn(SCH$_2$CH$_2$COOCH$_3$)$_3$
monobutyltin tris(2-ethylhexyl 3-mercaptopropionate),
dibutyltin bis(isooctyl mercaptoacetate),
dibutyltin bis(methyl 3-mercaptopropionate),
dibutyltin bis(2-ethylhexyl 3-mercaptopropionate),
dibutyltin bis(3-methoxybutyl 3-mercaptopropionate),
dioctyltin bis(methyl 3-mercaptopropionate), Oct$_2$Sn(SCH$_2$CH$_2$COOCH$_3$)$_2$
dioctyltin bis(2-ethylhexyl mercaptoacetate),
dioctyltin bis(isooctyl mercaptoacetate),
dioctyltin bis(isooctyl 3-mercaptopropionate),
diphenyltin bis(2-ethylhexyl 3-mercaptopropionate),
trioctyltin 2-ethylhexyl 3-mercaptopropionate,
tributyltin methyl 3-mercaptopropionate, Bu$_3$SnSCH$_2$CH$_2$COOCH$_3$
dibutyltin (methyl 3-mercaptopropionate) (laurate), $$Bu_2Sn\begin{cases} SCH_2CH_2COOCH_3 \\ OOCC_{11}H_{23} \end{cases}$$

dibutyltin (2-ethylhexyl 3-mercaptopropionate) (lauryl maleate), and
dioctyltin (2-ethylhexyl mercaptoacetate) (lauryl mercaptide).

The starting compound represented by the formula (2) may be exemplified by:
monobutyltin mono(methyl 3-mercaptopropionate) (sulfide), $$BuSn\begin{cases} SCH_2CH_2COOCH_3 \\ S \end{cases}$$

monobutyltin mono(isooctyl mercaptoacetate) (oxide),
monooctyltin mono(2-ethylhexyl 3-mercaptopropionate) (sulfide), and
monobutyltin mono(3-methoxybutyl 3-mercaptopropionate (maleate).

The starting compound represented by the formula (3) may be exemplified by:
bis(dibutyltin butyl mercaptoacetate)maleate $$Bu_2Sn\begin{cases} SCH_2COOBu \\ OCOCH \end{cases}$$
$$Bu_2Sn\begin{cases} OCOCH \\ SCH_2COOBu \end{cases}$$

bis(dibutyltin methyl mercaptoacetate)sulfide, $$Bu_2SnSCH_2COOCH_3 \\ | \\ S \\ | \\ Bu_2SnSCH_2COOCH_3$$

bis(dibutyltin 2-ethylhexyl 3-mercaptopropionate)oxide,
bis(monobutyltin butyl 3-mercaptopropionate laurate)-maleate.

In the above formulae, Bu, iso-Oct and Oct represent butyl, isooctyl and octyl, respectively.

Such starting alcohols as a monovalent aliphatic alcohol, a divalent aliphatic alcohol and an aliphatic alkoxyalkyl alcohol employed in this invention have higher boiling point than alcohols having the formula R$^4$OH to be removed from the starting alkyltin mercaptocarboxylic acid ester, and the difference of the boiling points between the alcohol introduced and the alcohol removed is at least about 30°C, preferably over about 50°C.

Generally, the alcohol employed in this invention may preferably be oleyl alcohol, lauryl alcohol, tridecyl alcohol, myristyl alcohol, cetyl alcohol and stearyl alcohol; ethylene glycol, propylene glycol, trimethylene glycol, 1,4-butanediol, 1,5-pentanediol and 1,6-hexanediol; and methoxypropanol, methoxybutanol, ethoxybutanol and butoxybutanol.

The alcohol employed in this invention may generally be employed in an almost equivalent amount to the starting ester. That is, in case one R$^4$ group is contained in the starting ester, the starting ester and the starting alcohol are used in approximately 1 : 1 molar ratio. In case two, three or four R$^4$ groups are contained in the starting ester, the starting ester and the starting alcohol are used in approximately 1 : 2, 1 : 3 or 1 : 4 molar ratio, respectively. However, if low interesterification ratio is desired, a smaller amount of the alcohol may be employed. For instance, two moles of the starting ester containing one R$^4$ group and one mole of the starting alcohol are reacted, there may be obtained up to 50 % interesterification ratio (based on the starting ester). On the other hand, in case such starting alcohol that is not harmful to a resin in which the stabilizer is incorporated and that acts as, for instance, a lublicant for the resin is employed, a larger amount of the alcohol (e.g., 1.5 – 3.0 moles per one mole of the ester containing one R$^4$ group) may be employed. Accordingly, the amount less than or extremely more than the equivalent amount may be adopted with reference to the purposes. Further, more than one kind of the alcohols may be together employed. The reaction temperature may generally be within 100°–200°C and preferably be within 120°–150°C.

During the interesterification reaction, R$^4$ alcohols are produced. These alcohols are removed during the reaction by distillation under atmospheric pressure or under reduced pressure depending upon the boiling points of the produced alcohols. After completion of the reaction, the unreacted alcohol and the excessive alcohol may be removed by distillation or may remain in the reaction product.

In general, the product thus obtained contains a large amount, for instance, more than 90 weight parts, of the molecular weight increased alkyltin mercaptocarboxylic acid ester and a small amount of the starting compounds. The molecular weight increased alkyltin mercaptocarboxylic acid ester may be exemplified as follows.

When the starting compounds of the formula (1) are used, the resultants may be;
monobutyltin tris(stearyl mercaptoacetate),
monobutyltin tris(oleyl 3-mercaptopropionate),
monooctyltin tris(tridecyl 3-mercaptopropionate), dibutyltin bis(stearyl 3-mercaptopropionate),
dibutyltin bis(oleyl 3-mercaptopropionate),
dibutyltin bis(isostearyl mercaptoacetate),
dibutyltin bis(myristyl 3-mercaptoacetate),
trioctyltin oleyl 2-methyl-3-mercaptopropionate,
dibutyltin (oleyl 3-mercaptopropionate) 13.70 maleate),
dioctyltin (stearyl mercaptoacetate) (stearyl maleate),
dibutyltin (tridecyl 3-mercaptopropionate) (benzoate). and
dioctyltin (lauryl 3-mercaptopropionate) (lauryl mercaptide).

When the starting compounds of the formula (2) are used, the resultants may be:
monobutyltin mono(oleyl 3-mercatopropionate sulfide,
monooctyltin mono(stearyl 3-mercaptopropionate)oxide. and
monobutyltin mono(oleyl mercaptoacetate)maleate, When the starting compounds of the formula (3) are used, the resultants may be:
bis(dibutyltin oleyl 3-mercaptopropionate) oxide,
bis(dibutyltin stearyl 3-mercaptopropionate)sulfide. and
bis(dioctyltin lauryl mercaptoacetate)maleate.

The product obtained in the present invention can be advantageously utilized as the stabilizer without purification, since there contains, as mentioned before, no catalyzer in the product.

Alkyltin mercaptocarboxylic acid ester obtained according to the present invention is utilized as a stabilizer for synthetic resins such as chlorine-containing resins, acrylonitrile — butadiene — styrene copolymers, methylmethacrylate — butadiene — styrene copolymers and the like. Chlorine-containing resins may be exemplified by a vinyl chloride resin, vinyl chloride — vinyl acetate copolymers, vinyl chloride — vinyl ether copolymers, vinyl chloride — vinylidene chloride copolymers, vinyl chloride — propylene copolymers, vinyl chloride — acrylonitrile copolymers, a chlorinated vinyl chloride resin, chlorinated polyethylene and the like.

The present invention will be more concretely illustrated by the following examples.

EXAMPLE 1

In a flask equipped with a stirrer, a thermometer and a cooler were placed 235.5 g (0.5 mol) of dibutyltin bis(methyl 3-mercaptopropionate) and 268.5 g (1 mol) of oleyl alcohol, and the mixture was heated with stirring. when the temperature of the solution was elevated to about 120°C, methyl alcohol began to distill out of the solution. The reaction was continued at a temperature in the range of 130°–140°C with distillation of methyl alcohol. About 5 hours later, the distillation of methyl alcohol almost ceased and 472.6 g of a pale yellow reaction product having little odor (principal ingredient: dibutyltin bis(oleyl 3-mercaptopropionate)) was obtained as a residue.

IR spectrum (liquid film) $\nu_{max}cm^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 1258% (by weight)

The methyl alcohol distilled was in an amount of 31.4 g (theoretical amount; 32.0 g). This shows that the ratio of ester interchange is 98.1%. The amounts of the methylester and oleylester contained in the reaction product which were determined by means of gas chromatography were 1.8 and 98.2 molar % respectively. This result is substantially consistent with the above-mentioned ratio of ester interchange.

EXAMPLE 2

In the similar flask, 200 g (0.3 mol) of dibutyltin bis(2-ethylhexyl 3(mercaptopropionate) and 162.3 g (0.6 mol) of stearyl alcohol were heated with stirring under reduced pressure (5 mm/Hg – 10 mm/Hg). At a temperature of about 120°C, there began distillation of 2-ethylhexyl alcohol. The reaction was continued at a temperature in the range of 130°to 140°C with distilling off 2-ethylhexyl alcohol produced. About 7 hours later, the distillation of 2-ethylhexyl alcohol almost ceased to give 288.2 g of a pale yellow reaction product having little odor (principal ingredient: dibutyltin bis(stearyl 3-mercaptopropionate)) as a residue.

IR spectrum (liquid film) $\nu_{max}cm^{-1}$: 510, 600, 720, 1050, 1150 – 1250, 1280 – 1300, 1350, 1460 – 1470, 1740, 2850, 2860, 2925, 2950, 3400 – 3500

Analysis for Sn content; 12.38% (by weight)

The 2-ethylhexyl alcohol distilled was in an amount of 74.1 g (theoretical amount: 78 g). This shows that the ratio of ester interchange is 94.9%. The amounts of the 2-ethylhexyl ester and stearyl ester contained in the reaction product which were determined by gas chromatography were 3.5 and 96.5 molar % respectively. This result is substantially consistent with the above-mentioned ratio of ester interchange.

EXAMPLE 3

In the similar flask, 319.5 g (0.5 mol) of dibutyltin bis(isooctyl mercaptoacetate) and 268.5 g (1 mol) of oleyl alcohol were caused to react under the same conditions as in example 2. There was obtained 461.9 g of a pale yellow reaction product having little odor (principal ingredient: dibutyltin bis(oleyl mercaptoacetate)).

IR spectrum (liquid film) $\nu_{max}cm^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 12.87% (by weight)

The isooctanol distilled was in an amount of 126.1 g (theoretical amount: 130 g). This shows that the ratio of ester interchange is 97.0%. The amounts of the isooctylester and oleylester contained in the reaction product which were determined by gas chromatography were 2.5 and 97.5 molar % respectively. This result is substantially consistent with the above-mentioned ratio of ester interchange.

EXAMPLE 4

In the similar flask, 224.7 g (0.3 mol) of monobutyltin tris(3-methoxybutyl 3-mercaptopropionate and 243.5 g (0.9 mol) of isostearyl alcohol were caused to react under the same conditions as in example 2. There was obtained 378.2 g of a pale yellow reaction product having little odor (principal ingredient; monobutyltin tris(isostearyl 3-mercaptopropionate)).

IR spectrum (liquid film) $\nu_{max}cm^{-1}$: 510, 600, 720, 1050, 1150 – 1250, 1280 – 1300, 1350, 1460 – 1470, 1740, 2850, 2860, 2925, 2950, 3400 – 3500

Analysis for Sn content: 9.43% (by weight)

The 3-methoxybutanol distilled was in an amount of 90.0 g (theoretical amount: 93.6 g). This shows that the ratio of ester interchange is 96.2%. The amounts of the 3-methoxybutylester and isostearylester contained in the reaction product which were determined by gas chromatography were 4.2 and 95.8 molar % respectively. This result is substantially consistent with the above-mentioned ratio of ester interchange.

EXAMPLE 5

In the similar flask, 266.8 g (0.4 mol) of dioctyltin bis(butyl 3-mercaptopropionate) and 214.8 g (0.8 mol) of oleyl alcohol were caused to react under the same conditions as in example 1. There was obtained 423.9 g of a pale yellow reaction product having little odor (principal ingredient; dioctyltin bis(oleyl 3-mercaptopropionate)).

IR spectrum (liquid film) $\nu_{max}\text{cm}^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 11.22% (by weight)

The butyl alcohol distilled was in an amount of 57.7 g (theroetical amount: 59.3 g). This shows that the ratio of ester interchange is 97.3%. The amounts of the butylester and oleylester contained in the reaction product which were determined by gas chromatography were 2.5 and 97.5 molar % respectively. This result is substantially consistent with the above-mentioned ratio of ester interchange.

EXAMPLE 6

In the similar flask, 291.5 g (0.5 mol) of dimethyltin bis(2-ethylhexyl 3-mercaptopropionate) and 200.4 g (1 mol) of tridecyl alcohol were caused to react under the same conditions as in example 2. There was obtained 368.4 g of a pale yellow reaction product having little odor (principal ingredient: dimethyltin bis(tridecyl 3-mercaptopropionate)).

IR spectrum (liquid film) $\nu_{max}\text{cm}^{-1}$: 510, 600, 720, 1050, 1150 – 1250, 1280 – 1300, 1350, 1460 – 1470, 1740, 2850, 2860, 2925, 2950, 3400 – 3500

Analysis for Sn content: 16.14% (by weight)

The 2-ethylhexyl alcohol distilled was in an amount of 123.5 g (theoretical amount: 130 g). This result shows that the ratio of ester interchange is 95.0%. The amounts of the 2-ethylhexylester and tridecylester contained in the reaction product which were determined by gas chromatography were 4.3 and 95.7 molar % respectively. This result is substantially consistent with the above-mentioned ratio of ester interchange.

EXAMPLE 7

In the similar flask, 277.5 g (0.5 mol) of dibutyltin bis(butyl 3-mercaptopropionate) and 45 g (0.5 mol) of 1,4-butanediol were caused to react under the same conditions in example 1. There was obtained a pale yellow reaction product having little odor (principal ingredient; dibutyltin 1,4-butanediol di-3-mercaptopropionate).

IR spectrum (liquid film) $\nu_{max}\text{cm}^{-1}$: 510, 600, 720, 1050, 1150 – 1250, 1280 – 1300, 1350, 1460 – 1470, 1740, 2850, 2860, 2925, 2950, 3400 – 3500

Analysis for Sn content: 23.64% (by weight)

The butyl alcohol distilled was in an amount of 71 g (theoretical amount: 74 g). This shows that the ratio of ester interchange is 96.0 %. The amounts of the butylester and 1,4-butanediolester contained in the reaction product which were determined by gas chromatography were 3.5 and 96.5 molar % respectively. This result is substantially consistent with the above-mentioned ratio of ester interchange.

EXAMPLE 8

In the similar flask, 184.6 g (0.37 mol) of dibutyltin bis(methyl 2-methyl-3-mercaptopropionate) and 198.7 g (0.74 mol) of oleyl alcohol were caused to react under the same conditions as in example 1. There was obtained 360.7 g of a pale yellow reaction product having little odor (principal ingredient: dibutyltin bis(oleyl 2-methyl-3-mercaptopropionate)).

IR spectrum (liquid film) $\nu_{max}\text{cm}^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 12.20 % (by weight)

The methanol distilled was in an amount of 22.6 g (theoretical amount: 23.7 g). This shows that the ratio of ester interchange is 95.4 %. The amounts of the methylester and oleylester contained in the reaction product which were determined by gas chromatography were 4.6 and 95.4 molar % respectively. This result is substantially consistent with the above-mentioned ratio of ester interchange.

EXAMPLE 9

In the similar flask, 154.8 g (0.25 mol) of dibutyltin bis(methyl 3-mercaptocinnamate) and 134.3 g (0.5 mol) of oleyl alcohol were caused to react under the same conditions as in example 1. There was obtained 274.6 g of a pale yellow reaction product having little odor (principal ingredient: dibutyltin bis(oleyl 3-mercaptocinnamate)).

IR spectrum (liquid film) $\nu_{max}\text{cm}^{-1}$: 510, 600, 690 – 710, 720, 730 – 770, 1050, 950 – 1250, 1280 – 1300, 1350, 1460 – 1470, 1580, 1600, 1650, 1700 – 2000, 2850, 2860, 2925, 2950, 3000 – 3100, 3400 – 3500

Analysis for Sn content: 10.82 % (by weight)

The methanol distilled was in an amount of 14.5 g (theoretical amount: 16.0 g). This shows that the ratio of ester interchange is 90.6 %. The amounts of the methylester and oleylester contained in the reaction product which were determined by gas chromatography were 8.2 and 91.8 molar % respectively. This result is substantially consistent with the above-mentioned ratio of ester interchange.

EXAMPLE 10

In the similar flask, 324.5 g (0.5 mol) of dibutyltin (2-ethylhexyl 3-mercaptopropionate) (laurate) and 134.3 g (0.5 mol) of oleyl alcohol were caused to react under the same conditions as in example 2. There was obtained 397.7 g of a pale yellow reaction product having little odor (principal ingredient; dibutyltin (oleyl 3-mercaptopropionate (laurate)).

IR spectrum (liquid film) $\nu_{max}\text{cm}^{-1}$ 510, 600, 720, 1050, 1150 – 1250, 1280 – 1300, 1350, 1460 – 1470, 1500 – 1600, 1650, 1740, 2850, 2860, 2925, 2950, 3000, 3400 – 3500

Analysis for Sn content: 14.95 % (by weight)

The 2-ethylhexyl alcohol distilled was in an amount of 61.1 g (theoretical amount; 65.1 g). This shows that the ratio of ester interchange is 93.9 %. The amounts of the 2-ethylhexylester and oleylester contained in the reaction product which were determined by gas chromatography were 5.0 and 95.0 molar % respectively. This result is substantially consistent with the above-mentioned ratio of ester interchange.

EXAMPLE 11

In the similar flask, 432.0 g (0.5 mol) of bis(di-butyltin 3-methoxybutyl 3-mercaptopropionate)oxide and 268.5 g (1 mol) of oleyl alcohol were caused to react under the same conditions as in example 2. There was obtained 604.7 g of a pale yellow reaction product having little odor (principal ingredient: bis(di-butyltin oleyl 3-mercaptopropionate)oxide).

IR spectrum (liquid film) $\nu_{max}cm^{-1}$ 510, 600, 720, 1050, 1150 – 1250, 1280 – 1300, 1350, 1460 – 1650, 1740, 2850, 2860, 2925, 2950, 3000, 3400 – 3500

Analysis for Sn content: 19.66 % (by weight) 92.1

The 3-methoxybutanol distilled was in an amount of 95.8 g (theoretical amount: 104 g). This shows that the ratio of ester interchange is 92.1%. The amounts of the 3-methoxybutylester and oleylester contained in the reaction product which were determined by gas chromatography were 5.5 and 94.5 molar % respectively. This result is substantially consistent with the above-mentioned ratio of ester interchange.

EXAMPLE 12

In the similar flask, 409.0 g (1 mol) of monobutyltin mono(2-ethylhexyl 3-mercaptopropionate)oxide and 242.5 g (1 mol) of hexadecyl alcohol were caused to react under the same conditions as in example 2. There was obtained 528.6 g of a pale yellow reaction product having little odor (principal ingredient; monobutyltin (hexadecyl 3-mercaptopropionate)oxide).

IR spectrum (liquid film) $\nu_{max}cm^{-1}$: 510, 600, 720, 1050, 1150 – 1250, 1280 – 1300, 1350, 1460 – 1470, 1740, 2850, 2860, 2925, 2950, 3400 – 3500

Analysis for Sn content: 22.49 % (by weight)

The 2-ethylhexylalcohol distilled was in an amount of 122.9 g (theoretical amount: 130.2 g). This shows that the ratio of ester interchange is 94.4 %. The amounts of the 2-ethylhexylester and hexadecylester contained in the reaction product which were determined by gas chromatography were 5.0 and 95.0 molar % respectively. This result is substantially consistent with the above-mentioned ratio of ester interchange.

EXAMPLE 13

In the similar flask, 308.5 g (0.5 mol) of monobutyltin tris(butyl mercaptoacetate) and 402.8 g (1.5 mol) of oleyl alcohol were caused to react under the same conditions as in example 1. There was obtained 600 g of a pale yellow reaction product having little odor (principal ingredient; monobutyltin tris(oleyl mercaptoacetate)).

IR spectrum (liquid film) $\nu_{max}cm^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 9.91% 9.91 weight)

The butyl alcohol distilled was in an amount of 108.2 g (theoretical amount: 111 g). This shows that the ratio of ester interchange is 97.5 %. The amounts of the butylester and oleylester contained in the reaction product which were determined by gas chromatography were 2.5 and 97.5 molar % respectively. This result is substantially consistent with the above-mentioned ratio of ester interchange.

EXAMPLE 14

In the similar flask, 84.3 g (0.1 mol) of bis(monobutyltin bis(methyl 3-mercaptopropionate))oxide and 107.4 g (0.4 mol) of oleyl alcohol were caused to react under the same conditions as in example 1. There was obtained 179.3 g of a pale yellow reaction product having little odor (principal ingredient: bis(monobutyltin bis(oleyl 3-mercaptopropionate))oxide).

IR spectrum (liquid film) $\nu_{max}cm^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 13.26% (by weight)

The methyl alcohol distilled was in an amount of 12.4 g (theoretical amount: 12.8 g). This shows that the ratio of ester interchange is 97 %. The amounts of the methylester and oleylester contained in the reaction product which were determined by gas chromatography were 2.5 and 97.5 molar % respectively. This result is substantially consistent with the above-mentioned ratio of ester interchange.

EXAMPLE 15

In the similar flask, 307.0 g (0.5 mol) of dibutyltin bis(3-methoxybutyl 3-mercaptopropionate) and 270.5 g (1.0 mol) of stearyl alcohol were caused to react under the same conditions as in example 2. There was obtained 478.3 g of a pale yellow reaction product having little odor (principal ingredient: dibutyltin bis(stearyl 3-mercaptopropionate)). IR spectrum (liquid film) $\nu_{max}cm^{116\ 1}$: 510, 600, 720, 1050, 1150 – 1250, 1280 – 1300, 1350, 1460 – 1470, 1740, 2850, 2860, 2925, 2950, 3400 – 3500

Analysis for Sn content: 12.43% (by weight)

The 3-methoxybutanol distilled was in an amount of 99.2 g (theoretical amount: 104 g). This shows that the ratio of ester interchange is 95.4 %. The amounts of the 3-methoxybutylester and stearylester contained in the reaction product which were determined by gas chromatography were 3.0 and 97.0 molar % respectively. This result is substantially consistent with the above-mentioned ratio of ester interchange.

EXAMPLE 16

In the similar flask, 389 g (0.5 mol) of dioctyltin bis(2-ethylhexyl 3-mercaptopropionate) and 268.5 g (1.0 mol) of oleyl alcohol were caused to react under the same conditions as in example 2. There was obtained 532.5 g of a pale yellow reaction product having little odor (principal ingredient: dioctyltin bis(oleyl 3-mercaptopropionate)).

IR spectrum (liquid film) $\nu_{max}cm^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 11.16 % (by weight)

The 2-ethylhexyl alcohol distilled was in an amount of 125.0 g (theoretical amount: 130.2 g). This shows that the ratio of ester interchange is 96.0 %. The amounts of the 2-ethylhexylester and oleylester contained in the reaction product which were determined by gas chromatography were 3.0 and 97.0 molar % respectively. This result is substantially consistent with the above-mentioned ratio of ester interchange.

EXAMPLE 17

In the similar flask, 291 g (0.5 mol) of dimethyltin bis(2-ethylhexyl 3-mercaptopropionate) and 268.5 g (1.0 mol) of oleyl alcohol were caused to react under the same conditions as in example 2. There was obtained 433.9 g of a pale yellow reaction product having little odor (principal ingredient: dimethyltin bis(oleyl 3-mercaptopropionate)).

IR spectrum (liquid film) $\nu_{max}$cm$^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 13.70% (by weight)

The 2-ethylhexyl alcohol distilled was in an amount of 125.6 g (theoretical amount: 130.2 g). This shows that the ratio of ester interchange is 96.5 %. The amounts of the 2-ethylhexylester and oleylester contained in the reaction product which were determined by gas chromatography were 3.2 and 96.7 molar % respectively. This result is substantially consistent with the above-mentioned ratio of ester interchange.

EXAMPLE 18

In the similar flask, 375 g (0.5 mol) of dioctyltin bis(isooctyl mercaptoacetate) and 268.5 g (1.0 mol) of oleyl alcohol were caused to react under the same conditions as in example 2. There was obtained 516.8 g of a pale yellow reaction product having little odor (principal ingredient. dioctyltin bis(oleyl mercaptoacetate)).

IR spectrum (liquid film) $\nu_{max}$cm$^{-1}$: 510, 600, 720, 1050, 1150 – 1250, 1280 – 1300, 1350, 1460 – 1470,1650, 1740, 2850, 2860, 2925, 2950, 3000, 3400 – 3500

Analysis for Sn content: 11.50 % (by weight)

The isooctanol distilled was in an amount of 126.7 g (theoretical amount: 130.2 g). This shows that the ratio of ester interchange is 97.3 %. The amounts of the isooctylester and oleylester contained in the reaction product which were determined by gas chromatography were 2.7 and 97.3 molar % respectively. This result is substantially consistent with the above-mentioned ratio of ester interchange.

EXAMPLE 19

In the similar flask, 311.4 g (0.5 mol) of dibutyltin bis(methyl 3-phenyl-3-mercaptopropionate) and 268.5 g (1.0 mol) of oleyl alcohol were caused to react under the same conditions as in example 2. There was obtained 548.4 g of a pale yellow reaction product having little odor (principal ingredient. dibutyltin bis(oleyl 3-phenyl-3-mercaptopropionate)).

IR spectrum (liquid film) $\nu_{max}$cm$^{-1}$: 510, 600, 690 – 710, 720, 730 – 770, 1050, 950 – 1250, 1280 – 1300, 1350, 1460 – 1470, 1580, 1600, 1650, 1700 – 2000, 2850, 2860, 2925, 2950, 3000 – 3100, 3400 – 3500

Analysis for Sn content: 10.48 % (by weight)

The methyl alcohol distilled was in an amount of 31.5 g (theoretical amount: g). This shows that the ratio of ester interchange is 98.5 %. The amounts of the methylester and oleylester contained in the reaction product which were determined by gas chromatography were 2.0 and 98.0 molar % respectively. This result is substantially consistent with the above-mentioned ratio of ester interchange.

EXAMPLE 20

In the similar flask, 307 g (0.5 mol) of dibutyltin bis(3-methoxybutyl 3-mercaptopropionate) and 268.5 g (1.0 mol) of oleyl alcohol were caused to react under the same conditions as in example 2. There was obtained 475.2 g of a pale yellow reaction product having little odor (principal ingredient: dibutyltin bis(oleyl 3-mercaptopropionate)).

IR spectrum (liquid film) $\nu_{max}$cm$^{-1}$: 510, 600, 720, 1050, 1150 – 1250, 1280 – 1300, 1350, 1460 – 1470, 1650, 1740, 2850, 2860, 2925, 2950, 3000, 3400 – 3500

Analysis for Sn content: 12.5 % (by weight)

The 3-methoxybutyl alcohol distilled was in an amount of 100.3 g (theoretical amount: 104 g). This shows that the ratio of ester interchange is 96.5 %. The amounts of the 3-methoxybutylester and oleylester contained in the reaction product which were determined by gas chromatography were 3.0 and 97.0 molar % respectively. This result is substantially consistent with the above-mentioned ratio of ester interchange.

EXAMPLE 21

Various experiments for the compounds prepared in examples 1 to 20 as to the properties of heat resistance, lubrication and odor were conducted.

Both dibutyltin bis(isooctyl mercaptoacetate) and dibutyltin bis(2-ethylhexyl 3-mercaptopropionate) were employed for comparison with the compounds prepared in examples 1, 2, 3, 7, 8, 11, 15, 19 and 20.

Both dioctyltin bis(isooctyl mercaptoacetate) and dioctyltin bis(2-ethylhexyl 3-mercaptopropionate) were employed for comparison with the compounds prepared in examples 5, 16 and 18.

Monobutyltin tris(butyl mercaptoacetate) was employed for comparison with the compounds prepared in examples 4, 12, 13 and 14.

Dimethyltin bis(2-ethylhexyl 3-mercaptopropionate) was employed for comparison with the compounds prepared in examples 6 and 17.

Both dibutyltin bis(methyl 3-mercaptocinnamate) and dibutyltin (2-ethylhexyl 3-mercaptopropionate) (laurate) were employed for comparison with the compounds prepared in examples 9 and 10.

Each of the above-mentioned compounds to be employed for the comparison purpose (3.0 weight parts) was incorporated into 100 weight parts of polyvinyl chloride resin ($\overline{P}$ = 800). Into the same resin was incorporated the compound prepared in each of the examples in the such amount that the Sn content in the obtained resin composition comprising the tested compound is the same as that in the resin composition comprising compound to be employed for comparison.

The obtained resin compositions were kneaded on the hot roller at a temperature of 175°C for 5 minutes. The judgement of lubrication was made by observing the degree of the ease in removal of the rolled sheet from the hot roller. The compounds according to the present invention are superior in the lubrication to the compounds employed for the comparison purpose.

As to odor emitted in the hot rolling process and/or remaining in the sheet, the compounds of the present invention are also superior to the compounds employed for the comparison purpose.

Comparison as to the heat stability was made in the following manner; the kneaded sheet was cut into segments which were then heated by Geer's oven set at the temperature of 180°C. The sheet under heating was taken out at regular intervals, and observed. There were not noticeable difference between the sheets comprising the compounds of the present invention and those comprising the compounds employed for the comparison purpose.

What is claimed is:

1. A process for the preparation of a stabilizer for synthetic resins mainly a consisting of a molecular weight increased alkyltin mercaptocarboxylic acid ester which is characterized by reaccting an alkyltin mercaptocarboxylic acid alkylester having a formula selected from the group consisting of reacting

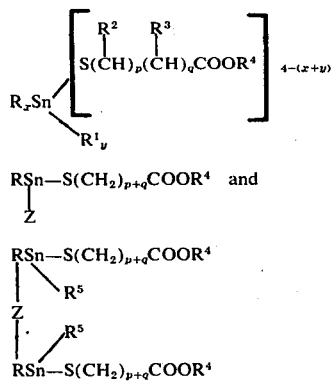

in which R is selected from the group consisting of an aliphatic alkyl group having 1 – 12 carbon atoms and a phenyl group; $R^1$ is selected from the group consisting of an aliphatic alkylthio group having 8 – 18 carbon atoms, an aliphatic alkanoyloxy group having 8 – 18 carbon atoms, a residue of a monoalkylester of maleic acid in which the alkyl is an aliphatic alkyl containing 8 – 18 carbon atoms and a benzoyloxy group; $R^2$ and $R^3$ are the same or different and each is selected from the group consisting of hydrogen, an aliphatic alkyl group having 1 – 4 carbon atoms and a phenyl group; $R^4$ is selected from the group consisting of an aliphatic alkyl group having 1 – 8 carbon atoms and an aliphatic alkoxyalkyl group having 3 – 6 carbon atoms; $R^5$ is selected from the group consisting of an aliphatic alkyl group having 1 – 12 carbon atoms, an aliphatic alkanoyloxy group having 8 – 18 carbon atoms and a -$S(CH_2)_{p+q}COOR^4$ group; x and y are integers of 1 to 3 and 0 to 1, respectively, in which x+y is up to 3 inclusive; p and q are integers of 1 to 2 and 0 to 1, respectively; and Z is selected from the group consisting of oxygen, sulfur and a divalent maleic acid residue,
with a monovalent aliphatic alcohol having 4 – 18 carbon atoms, a divalent aliphatic alcohol having 2 – 6 carbon atoms or an aliphatic alkoxyalkyl alcohol having 4 – 10 carbon atoms, the boiling point of said alcohol being higher than that of an alcohol having the formula $R^4OH$, in which $R^4$ is the same as above, by at least 30°C,
at a temperature of 100° to 200°C in the absence of a catalyst, with removal of the lower boiling alcohol produced.

2. The process for the preparation of a stabilizer as claimed in claim 1, in which the starting alkyltin mercaptocarboxylic acid alkylester is represented by the formula

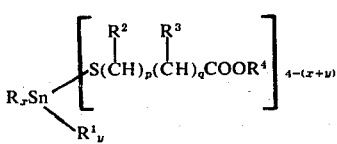

in which R, $R^1$, $R^2$, $R^3$, $R^4$, x, y, p and q have the same meanings as defined in claim 1.

3. The process for the preparation of a stabilizer as claimed in claim 2, in which a monovalent aliphatic alcohol having 12 – 18 carbon atoms is employed as the starting alcohol.

4. The process for the preparation of a stabilizer as claimed in claim 2, in which the starting alkyltin mercaptocarboxylic acid alkylester wherein $R^2$ and $R^3$ are both hydrogens is employed.

5. The process for the preparation of a stabilizer as claimed in claim 1, in which the starting alkyltin mercaptocarboxylic acid alkylester is represented by the formula

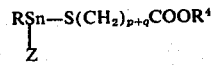

in which p+q is 2, Z is oxygen, and R and $R^4$ have the same meanings as defined in claim 1.

6. The process for the preparation of a stabilizer as claimed in claim 1, in which the starting alkyltin mercaptocarboxylic acid alkylester is represented by the formula

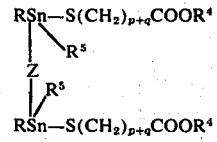

in which p+q is 2, Z is oxygen, and R, $R^4$ and $R^5$ have the same meanings as defined in claim 1.

7. The process for the preparation of a stabilizer as claimed in claim 1, in which the reaction is carried out to reach more than 90 % of molar interesterification ratio based on the amount of the starting alkyltin mercaptocarboxylic acid alkylester.

8. The process for the preparation of a stabilizer as claimed in claim 1, in which the reaction is carried out at a temperature ranging from 100° to 200°C.

9. The process for the preparation of a stabilizer as claimed in claim 1, in which the reaction is carried out at a temperature ranging from 120° to 150°C.

10. The process for the preparation of a stabilizer as claimed in claim 1, in which an amount of the starting alcohol almost equivalent to the starting ester is adopted.

11. The process for the preparation of a stabilizer as claimed in claim 1, in which the boiling point of the starting alcohol is higher than that of an alcohol having the formula $R^4OH$, in which $R^4$ has the meaning as defined in claim 1, by at least 50°C.

* * * * *

UNITED STATES PATENT OFFICE
CERTIFICATE OF CORRECTION

PATENT NO. : 3,962,296
DATED : June 8, 1976
INVENTOR(S) : TETSUO CHIBA et al

It is certified that error appears in the above-identified patent and that said Letters Patent are hereby corrected as shown below:

Column 7, line 6: replace "13.70" with ---(oleyl---.

Column 7, line 15: replace "mercatopropionate" with ---mercaptopropionate)---.

Column 7, line 51: replace "when" with --- When ---.

Column 11, line 11: replace "1460-1650" with ---1460-1470, 1650,---.

Column 11, line 13: delete "92.1".

Column 11, line 56: replace "9.91% 9.91 weight)" with ---9.91% (by weight)---.

Column 12, line 28: replace "$cm^{16}$ 1" with ---$cm^{-1}$---.

Column 14, last line: after "mainly", delete "a".

UNITED STATES PATENT OFFICE
CERTIFICATE OF CORRECTION

PATENT NO. : 3,962,296
DATED : June 8, 1976
INVENTOR(S) : TETSUO CHIBA et al

It is certified that error appears in the above-identified patent and that said Letters Patent are hereby corrected as shown below:

Column 3, line 31: replace "ENBODIMENTS" with ---EMBODIMENTS---.

Column 6, line 40: replace "lublicant" with --- lubricant ---.

Column 10, line 35 and Column 13, line 48: replace "950 - 1250" with ---1150 - 1250---.

Column 12, line 5: replace "))oxide)" with ---)oxide)---.

Signed and Sealed this second Day of August 1977

[SEAL]

Attest:

RUTH C. MASON
*Attesting Officer*

C. MARSHALL DANN
*Commissioner of Patents and Trademarks*